United States Patent
Hara et al.

(10) Patent No.: US 10,809,265 B2
(45) Date of Patent: Oct. 20, 2020

(54) METHOD FOR ESTIMATING NUMBER OF PODOCYTES IN URINE

(71) Applicants: Denka Company Limited, Tokyo (JP); Denka Seiken Co., Ltd., Tokyo (JP); Masanori Hara, Niigata (JP)

(72) Inventors: Masanori Hara, Niigata (JP); Hiroyuki Kurosawa, Tokyo (JP); Yoshiaki Hirayama, Tokyo (JP)

(73) Assignees: Masanori Hara, Niigata-Shi, Niigata (JP); DENKA COMPANY LIMITED, Chuo-Ku, Tokyo (JP)

( * ) Notice: Subject to any disclaimer, the term of this patent is extended or adjusted under 35 U.S.C. 154(b) by 220 days.

(21) Appl. No.: 15/567,903

(22) PCT Filed: Apr. 21, 2016

(86) PCT No.: PCT/JP2016/062648
§ 371 (c)(1),
(2) Date: Oct. 19, 2017

(87) PCT Pub. No.: WO2016/171216
PCT Pub. Date: Oct. 17, 2016

(65) Prior Publication Data
US 2018/0120324 A1    May 3, 2018

(30) Foreign Application Priority Data

Apr. 22, 2015 (JP) ................. 2015-087232

(51) Int. Cl.
*G01N 33/68* (2006.01)
*G01N 1/28* (2006.01)
*G01N 33/53* (2006.01)

(52) U.S. Cl.
CPC ............... *G01N 33/68* (2013.01); *G01N 1/28* (2013.01); *G01N 33/6893* (2013.01); *G01N 33/53* (2013.01); *G01N 2333/47* (2013.01); *G01N 2800/347* (2013.01)

(58) Field of Classification Search
None
See application file for complete search history.

(56) References Cited

U.S. PATENT DOCUMENTS

| 2004/0058395 A1* | 3/2004 | Hara ................ G01N 33/6893 435/7.1 |
| 2010/0233738 A1 | 9/2010 | Hara et al. |

OTHER PUBLICATIONS

Hara et al. "Urinary Sediment Podcalyxin (u-sed-PCX) Indicates Estimated Urinary Podocyte Number (eUPN) in Diabetic Nephropathy", J Am Soc Nephrol vol. 25, 2014, Abstract Edition, TH-PO413 (one page) (Year: 2014).*
Hara et al. "Urinary podocalyxin is an early marker for podocyte injury in patients with diabetes: establishment of a highly sensitive ELISA to detect urinary podocalyxin", Diabetologia (2012) 55:2913-2919 DOI 10.1007/s00125-012-2661-7 (Year: 2012).*
Kanno et al. "Urinary Sediment Podocalyxin in Children with Glomerular Diseases" Nephron Clin Pract 2003;95:c91-c99, DOI: 10.1159/000074322 (Year: 2003).*
Kanno et al. "Urinary Sediment Podocalyxin in Children with Mesangial Proliferative Glomerulonephritis", Niigata Medical Journal, 2002, vol. 116, No. 5, pp. 219-227, English abstract only (Year: 2002).*
Hara et al. "Apical Cell Membranes Are Shed into Urine from Injured Podocytes: A Novel Phenomenon of Podocyte Injury" J Am Soc Nephrol 16: 408-416, 2005 (Year: 2005).*
Hara et al. "Podocyte membrane vesicles in urine originate from tip vesiculation of podocyte microvilli" Human Pathology (2010) 41, 1265-1275 (Year: 2010).*
Asao, Rin et al., "Relationships between Levels of Urinary Podocalyxin, Number of Urinary Podocytes, and Histologic Injury in Adult Patients with IgA Nephropathy," Clinical Journal of the American Society of Nephrology, vol. 7, No. 9, pp. 1385-1393, Jun. 14, 2012.

* cited by examiner

*Primary Examiner* — Christine Foster
(74) *Attorney, Agent, or Firm* — Nixon & Vanderhye P.C.

(57) ABSTRACT

The present invention relates to a method of estimating the number of urinary podocytes, including detecting podocalyxin in a urinary sediment sample liquid, and more specifically, to a method of estimating the number of urinary podocytes, including the following steps (1) to (3): (1) a step of preparing the urinary sediment sample liquid by separating urinary sediment from urine collected from a test subject and solubilizing podocalyxin in the urinary sediment; (2) a step of calculating a podocalyxin excretion amount in the urinary sediment sample liquid through detection of podocalyxin in the urinary sediment sample liquid; and (3) a step of calculating the number of urinary podocytes by dividing the podocalyxin excretion amount in the urinary sediment sample liquid by a podocalyxin amount per podocyte.

8 Claims, 1 Drawing Sheet

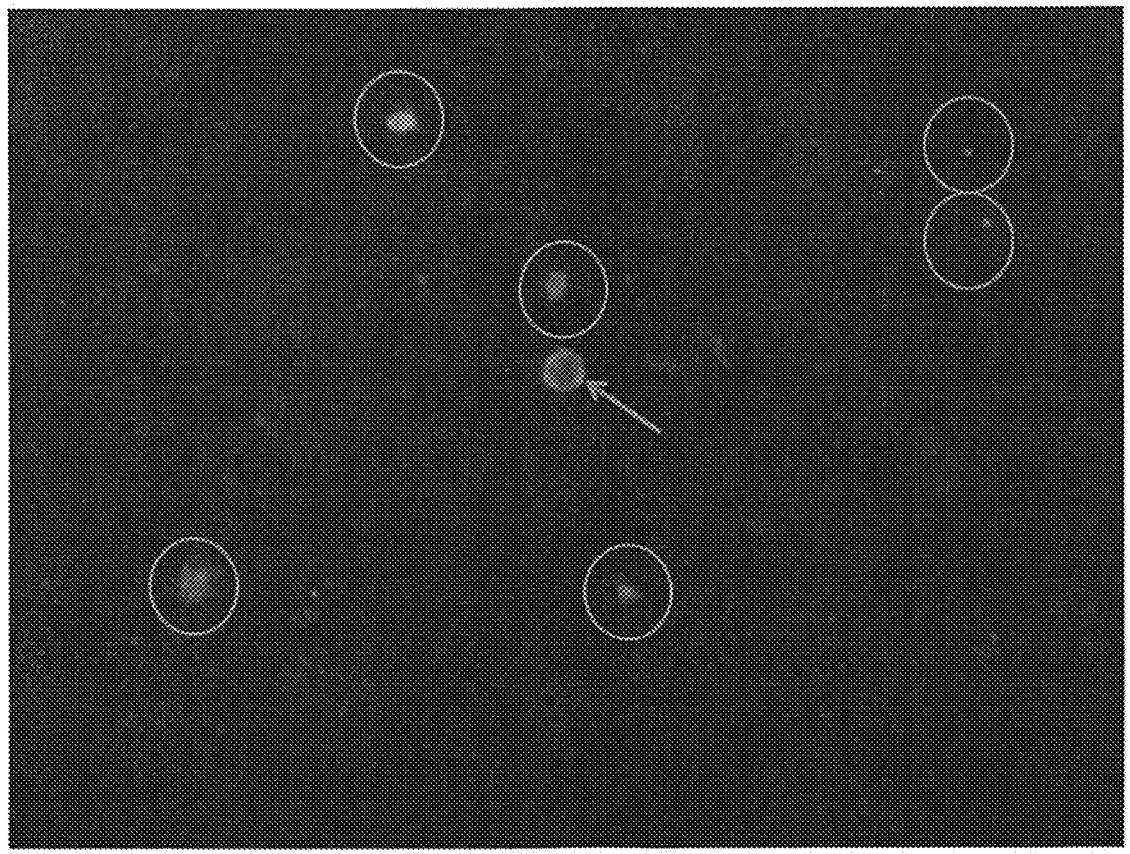
a fluorescent antibody method
using an anti-podocalyxin antibody
○: Fragments originated from podocyte
arrow: podocyte ly, it is considered that when appropriate treatment is properly performed for CKD patients depending on their progression stages, the number of patients subjected to dialysis and the number of patients who die of CVD can be reduced to a great extent.

METHOD FOR ESTIMATING NUMBER OF PODOCYTES IN URINE

TECHNICAL FIELD

The present invention relates to a method of estimating the number of urinary podocytes, including calculating the number of urinary podocytes through detection of podocalyxin in a urinary sediment sample liquid.

The present application claims priority from Japanese Patent Application No. 2015-087232, which is incorporated herein by reference.

BACKGROUND ART

The number of end-stage kidney disease (ESKD) patients requiring dialysis and transplantation has been increasing worldwide. The number of ESKD patients increased from 430,000 to 1,065,000 over 10 years from 1990 to 2000, and further increased to at least about 1, 650, 000 in 2008. In 2011, the number of maintenance dialysis patients in Japan reached about 300,000, and the number of the patients per million population is 2,126, which is the second largest in the world. The number of patients with chronic kidney disease (CKD), which progresses to ESKD, has also been increasing worldwide, and the number of CKD patients in the United States in 2000 is estimated to be 13.07% of an adult population (25,610,000 patients). The number of CKD patients in Japan in 2005 is 12.9% of an adult population (13,300,000 patients). In addition, CKD is a risk factor for cardiovascular disease (CVD). Out of CKD patients in Europe and the United States, the number of patients who die of CVD is larger than the number of patients subjected to dialysis. Also in Japan, CKD is a risk factor for CVD (Non Patent Literature 1). Accordingly, it is considered that when appropriate treatment is properly performed for CKD patients depending on their progression stages, the number of patients subjected to dialysis and the number of patients who die of CVD can be reduced to a great extent.

Podocalyxin is a glycoprotein that is present on surfaces of podocytes constructing the renal glomerulus and is responsible for a filtration function. The podocytes are located on a Bowman's space side in glomerular basement membrane and play important roles in a mechanism of glomerular filtration. A healthy subject has two kidneys, and there is a report that there are 600,000 glomeruli in each kidney with 300 podocytes per glomerulus (Non Patent Literature 2). Grasping of a degree of podocyte injury has an extremely important meaning in a renal disease (Non Patent Literature 3). Thus, in order to perform a nephropathy examination, podocalyxin to be excreted into urine is detected. There is a disclosure of simple means for examining nephropathy involving measuring urinary podocalyxin (Patent Literature 1).

As one of the renal diseases, there is known diabetic nephropathy. It is considered that loss of podocytes present in glomeruli of the kidneys contributes profoundly to progression of diabetic nephropathy (Non Patent Literature 3). The loss of podocytes from glomeruli is caused by detachment and shedding of podocytes from the glomerular basement membrane, and the detached and shed podocytes appear in urine. The podocytes shed into urine may serve as an indicator of severity in diabetic nephropathy.

At present, urinary podocytes are detected by a fluorescent antibody method. The inventors of the present invention have also succeeded in detecting podocytes by the fluorescent antibody method with use of an antibody against podocalyxin (PCX) serving as a podocyte marker (Non Patent Literature 4). The related-art fluorescent antibody method has confirmed appearance of 0.1 to 0.3 podocyte per mL of urine in patients with diabetic nephropathy. In addition, there is a report that the number of podocytes per glomerulus reduced from 544 to 475 over 3 years in diabetes patients having proteinuria (microalbuminuria and macroalbuminuria (hereinafter sometimes referred to as "micro/macroalbuminuria") (Non Patent Literature 5). In recent years, there has been proposed the new idea that the shedding of podocytes from glomeruli is caused by an aberration in mitosis of the podocytes (Non Patent Literature 6). In Non Patent Literature 6, it is suggested that podocytes undergoing aberrant mitosis eventually fall into cell death, resulting in disintegration of the cells.

It is desired that an efficient renal disease examination be performed by more accurately grasping the number of podocytes shed from glomeruli.

CITATION LIST

Patent Literature

[PTL 1]WO 2002/037099 A1

Non Patent Literature

[NPL 1]Edited by Japanese Society of Nephrology, Clinical Practice Guidebook for Diagnosis and Treatment of CKD 2012, p. 5, 7
[NPL 2]Vogelmann S U, Nelson W J, Myers B D. Et al. Urinary excretion of viable podocytes in health and renal disease. Am J Physiol Renal Physiol 2003; 285: F40-48.
[NPL 3]Pagtalunan M E, Miller P L, Jumping-Eagle S. et al. Podocyte loss and progressive glomerular injury in type II diabetes. J Clin Invest 1997; 99: 342-348.
[NPL 4]Hara M, Yanagihara T, Takada T. et al. Urinary excretion of podocytes reflects disease activity in children with glomerulonephritis. Am J Nephrol 1998; 18: 35-41.
[NPL 5]White K E, Bilous R W, Marshall S M, El Nahas M, Remuzzi G, Piras G, De Cosmo S, Viberti G. Podocyte number in normotensive type 1 diabetic patients with albuminuria. Diabetes. 2002 Oct.; 51(10): 3083-9.
[NPL 6]Lipias H, Romagnami P, Anders H-J. New insight into the pathology of podocyte loss Mitotic catastrophe. Am j Pathol 2013; 183: 1364-1374

SUMMARY OF INVENTION

Technical Problem

An object of the present invention is to provide a method of estimating the number of urinary podocytes more accurately and more simply than a related-art method.

Solution to Problem

The inventors of the present invention have made extensive investigations in order to achieve the above-mentioned object, and as a result, have confirmed that fragments of podocytes are detected in a urinary sediment sample acquired from a diabetic nephropathy patient, and have focused attention on the following matter: the number of urinary podocytes can be estimated by measuring a podocalyxin excretion amount in a urinary sediment sample liquid and using the podocalyxin excretion amount and a podocalyxin amount per podocyte. Thus, the inventors have completed the present invention.

That is, the present invention includes the following.

1. A method of estimating the number of urinary podocytes, including detecting podocalyxin in a urinary sediment sample liquid.

2. A method of estimating the number of urinary podocytes according to Item 1, further including calculating the number of urinary podocytes through use of a podocalyxin excretion amount in the urinary sediment sample liquid and a podocalyxin amount per podocyte.

3. A method of estimating the number of urinary podocytes according to Item 1 or 2, in which the urinary sediment sample liquid includes a urinary sediment sample liquid obtainedby separating urinary sediment from urine collected from a test subject and solubilizing podocalyxin in the urinary sediment.

4. A method of estimating the number of urinary podocytes according to any one of Items 1 to 3, in which the method includes the following steps:

(1) a step of preparing the urinary sediment sample liquid by separating urinary sediment from urine collected from a test subject and solubilizing podocalyxin in the urinary sediment;

(2) a step of calculating a podocalyxin excretion amount in the urinary sediment sample liquid through detection of podocalyxin in the urinary sediment sample liquid; and (3) a step of calculating the number of urinary podocytes by dividing the podocalyxin excretion amount in the urinary sediment sample liquid by a podocalyxin amount per podocyte.

5. An examination method for a renal disease, including using, as an indicator, the number of urinary podocytes obtained by the method of estimating the number of urinary podocytes of any one of Items 1 to 4.

6. A urine treatment method for detecting podocalyxin in a urinary sediment sample liquid, the urine treatment method including the following steps (a) to (c):

(a) a step of adding and mixing a buffer and a chelating agent into urine collected from a test subject;

(b) a step of centrifuging a solution obtained in the step (a) to separate urinary sediment; and (c) a step of adding and mixing a buffer, a chelating agent, and a surfactant into the urinary sediment obtained in the step (b).

7. A reagent kit for urine treatment, for detecting podocalyxin in a urinary sediment sample liquid, the reagent kit including the following (a) to (c):

(a) a treatment liquid 1 containing a buffer and a chelating agent;

(b) a treatment liquid 2 containing a buffer, a chelating agent, and a surfactant; and (c) an anti-podocalyxin antibody.

Advantageous Effects of Invention

According to the present invention, the number of urinary podocytes is estimated through detection of podocalyxin in the urinary sediment sample liquid, and thus the number of urinary podocytes can be estimated more easily and more accurately than by the related-art detection method for urinary podocytes using a fluorescence microscope. In addition, the use of the number of urinary podocytes obtained by the method of estimating the number of urinary podocytes of the present invention makes it possible to more accurately perform the evaluation of the onset of a renal disease, the evaluation of a therapeutic effect on the renal disease, the evaluation of the degree of podocyte injury, and the prediction of the prognosis of the renal disease.

BRIEF DESCRIPTION OF DRAWINGS

FIG. 1 is a micrograph obtained by staining podocalyxin in urinary sediment derived from a diabetic nephropathy patient by a fluorescent antibody method using an anti-podocalyxin antibody (Reference Example 1).

DESCRIPTION OF EMBODIMENTS

The present invention relates to a method of estimating the number of urinary podocytes, including detecting podocalyxin in a urinary sediment sample liquid. The podocytes are glomerular epithelial cells in the kidneys, are located on the Bowman's space side in the glomerular basement membrane, and play important roles in the mechanism of glomerular filtration. The grasping of the degree of podocyte injury is extremely important in the diagnosis of a renal disease. In particular, it has been foundthat the shedding of podocytes into urine occurs in a glomerular disease. Accordingly, a renal disease can be detected by confirming the presence or absence of urinary podocytes, and the number of urinary podocytes is considered to serve as an indicator of the severity of the renal disease. In urine, in particular, in urinary sediment, podocyte-derived fragments, as well as podocytes, are present (FIG. 1). In order to grasp the true total number of podocytes shed from the kidneys, it is necessary to estimate how large the number of podocytes from which the fragments of podocytes are derived is. When the number of podocytes shed from the kidneys to be excreted into urine (number of urinary podocytes) is accurately grasped, the diagnosis of a renal disease can be precisely performed.

The method of estimating the number of urinary podocytes of the present invention more specifically includes the following steps (1) to (3):

(1) a step of preparing the urinary sediment sample liquid by separating urinary sediment from urine collected from a test subject and solubilizing podocalyxin in the urinary sediment;

(2) a step of calculating a podocalyxin excretion amount in the urinary sediment sample liquid through detection of podocalyxin in the urinary sediment sample liquid; and (3) a step of calculating the number of urinary podocytes by dividing the podocalyxin excretion amount in the urinary sediment sample liquid by a podocalyxin amount per podocyte.

Herein, the urinary sediment sample liquid is prepared from a urine specimen collected from the test subject. The urine serving as the specimen may be obtained from any test subject, but is preferably obtained from a patient affected with diabetes or a renal disease (nephropathy). The diagnosis of diabetes and the renal disease may be performed by hitherto known means. A method of collecting the urine is not limited, but early morning urine or spot urine is preferably used. In addition, the volume of the urine required for the examination method of the present invention is from about 10 µL to about 2,000 µL.

In the present invention, in order to prepare the urinary sediment sample liquid, the urine serving as the specimen is treated with two kinds of treatment liquids by means including the following four steps (a) to (d).

The step (a) is a step including adjusting the pH of the urine and masking substances contained in urinary sediment except for podocytes and fragments of podocytes. This step is performed by adding and mixing, into the urine, a treatment liquid 1 capable of adjusting the pH of the urine and masking the substances other than the podocytes and the fragments of podocytes contained in the urinary sediment. The treatment liquid 1 may be any treatment liquid as long as the purpose of this step can be achieved, but is preferably exemplified by a solution obtained by adding, for example, a chelating agent to a buffer. The buffer and the chelating agent are not particularly limited as long as the purpose of this step can be achieved, and known ones may be used.

Herein, the buffer may be any buffer, but may be exemplified by Good's buffer. The Good's buffer may be exemplified by N-(2-acetamido)-2-aminoethanesulfonic acid (ACES), N-(2-acetamido)iminodiacetic acid (ADA), N,N-bis(2-hydroxyethyl)-2-aminoethanesulfonic acid (BES), N,N-bis(2-hydroxyethyl)glycine (Bicine), bis(2-hydroxyethyl)iminotris(hydroxymethyl)methane (Bis-Tris), N-cyclohexyl-3-aminopropanesulfonic acid (CAPS), N-cyclohexyl-2-aminoethanesulfonic acid (CHES), 3-[4-(2-hydroxyethyl)-1-piperazinyl]propanesulfonic acid (EPPS), 2-[4-(2-hydroxyethyl)-1-piperazinyl]ethanesulfonic acid (HEPES), 2-hydroxy-3-[4-(2-hydroxyethyl)-1-piperazinyl]propanesulfonic acid (HEPPSO), 2-morpholinoethanesulfonic acid (MES), 3-morpholinopropanesulfonic acid (MOPS), 2-hydroxy-3-morpholinopropanesulfonic acid (MOPSO), piperazine-1,4-bis(2-ethanesulfonic acid) (PIPES), piperazine-1,4-bis(2-hydroxy-3-propanesulfonic acid) (POPSO), N-tris(hydroxymethyl)methyl-3-aminopropanesulfonic acid (TAPS), 2-hydroxy-N-tris(hydroxymethyl)methyl-3-aminopropanesulfonic acid (TAPSO), N-tris(hydroxymethyl)methyl-2-aminoethanesulfonic acid (TES), N-[tris(hydroxymethyl)methyl]glycine (Tricine), 2-amino-2-hydroxymethylpropane-1,3-diol (Tris), Bis-Tris propane, cholamine chloride, glycinamide, 3-[N,N-bis(2-hydroxyethyl)amino]-2-hydroxypropanesulfonic acid (DIPSO), and N-cyclohexyl-3-aminopropanesulfonic acid (CAPSO), and may be prepared by adjusting the pH with NaOH or HCl. The Good's buffer has high buffering ability and hence enables efficient urine pH correction and homogenization.

Examples of the chelating agent as used herein may include, but not limited to, ethylenediamine-N,N,N',N'-tetraacetic acid (EDTA), O,O'-bis(2-aminoethyl)ethylene glycol-N,N,N',N'-tetraacetic acid (EGTA), O,O'-bis(2-aminophenyl)ethylene glycol-N,N,N',N'-tetraacetic acid, N,N-bis(2-hydroxyethyl)glycine, trans-1,2-diaminocyclohexane-N,N,N',N'-tetraacetic acid, diethylenetriamine-N,N,N',N'',N'''-pentaacetic acid, ethylenediamine-N,N'-dipropionic acid, N-(2-hydroxyethyl)iminodiacetic acid, iminodiacetic acid, nitrilotriacetic acid), nitrilotris(methylphosphonic acid), N,N,N',N'-tetrakis(2-pyridylmethyl)ethylenediamine, triethylenetetramine-N,N,N',N'',N''',N''''-hexaacetic acid, heparin, sodium citrate, sodium fluoride, acid citrate dextrose, and adenosine triphosphate. EDTA is preferred for the reason of high masking effects on urinary calcium and urinary magnesium.

In the treatment liquid 1 as used herein, the concentration of the buffer is from 0.05 M to 1 M, preferably from 0.1 M to 0.5 M, and the concentration of the chelating agent is from 0.001 M to 0.1 M, preferably from 0.005 M to 0.05 M. The treatment liquid 1 may contain, in addition to the buffer and the chelating agent, anything that does not impair the purpose of the step (a), but may not contain a surfactant. The treatment liquid 1 as used herein contains an additive, such as a preservative or an antiseptic, in some cases. The antiseptic encompasses, but not limited to, isothiazolone-based antiseptics, such as 5-chloro-2-methyl-4-isothiazolin-3-one and 2-methyl-4-isothiazolin-3-one, as well as sodium azide. More specifically, the treatment liquid 1 is exemplified by a solution containing 0.2 M EDTA in 2 M TES-NaOH (pH 7.0).

The step (b) is a step of centrifuging the solution obtained in the step (a) to collect the podocytes and the fragments of podocytes. The centrifugation in this step may be performed through use of a centrifuge with a gravity acceleration (G) set to from 500 g to 10,000 g, preferably from 800 g to 2,500 g. The target product of this step is sediment obtained after the centrifugation, and contains the podocytes and the fragments of podocytes. In this step, after the centrifugation, the supernatant is discarded and the sediment is collected. The resultant sediment is referred to as "urinary sediment" in the present invention.

The step (c) is a step including solubilizing podocalyxin expressed in the podocytes and the fragments of podocytes in the urinary sediment obtained in the step (b), adjusting the pH of the urinary sediment, and further masking substances contained in the urinary sediment except for the podocytes and the fragments of podocytes. This step is performed by adding and mixing, into the sediment, a treatment liquid 2 capable of solubilizing podocalyxin expressed in the podocytes and the podocyte fragments, adjusting the pH of the urinary sediment, and masking the substances contained in the urinary sediment except for the podocytes and the fragments of podocytes. The treatment liquid 2 may be any treatment liquid as long as the purpose of this step can be achieved, but is preferably exemplified by a solution obtained by adding, for example, a chelating agent and a surfactant to a buffer. The buffer, the chelating agent, and the surfactant are not particularly limited as long as the purpose of this step can be achieved, and known ones may be used.

Specific examples of the buffer and the chelating agent contained in the treatment liquid 2 are as described above. The surfactant contained in the treatment liquid 2 may be a nonionic surfactant or any of ionic surfactants, such as an anionic surfactant, a cationic surfactant, and an amphoteric surfactant, but is preferably a nonionic surfactant. Examples of the nonionic surfactant may include the following:

a polyoxyalkylene ether compound, such as a polyoxyethylene alkyl ether, a polyoxypropylene alkyl ether, a polyoxypropylene alkylphenyl ether, polyoxyethylene polystyryl phenyl ether, or polyoxyethylene polyoxypropylene glycol;

a polyhydric alcohol partial ester compound, such as a glycerin fatty acid partial ester, a sorbitan fatty acid partial ester, a pentaerythritol fatty acid partial ester, a propylene glycol mono fatty acid ester, or a sucrose fatty acid partial ester;

a polyoxyethylenated polyhydric alcohol fatty acid ester, such as a polyoxyethylene sorbitan fatty acid partial ester, a polyoxyethylene sorbitol fatty acid partial ester, a polyoxyethylene glycerin fatty acid partial ester, a polyethylene glycol fatty acid ester, a polyglycerin fatty acid partial ester, or polyoxyethylenated castor oil; and an amide or amine compound, such as a fatty acid diethanolamide, an N,N-bis-2-hydroxyalkylamine, a polyoxyethylene alkylamine, a triethanolamine fatty acid ester, or a trialkylamine oxide.

More specific examples of the nonionic surfactant include polyoxyethylenesorbitanmonolaurate, polyoxyethylenesorbitanoleate, octylphenoxypolyethoxyethanol, polyoxyethylene alkyl (12 to 14) ethers, polyethylene glycol lauryl ether, and diethylene glycol monohexadecyl ether. Such nonionic surfactants are commercially available as Tween (trademark) 20 (manufactured by Tokyo Chemical Industry Co., Ltd.), Tween (trademark) 80 (manufactured by Tokyo Chemical Industry Co., Ltd.), Triton (trademark) X-100 (manufactured by Roche Applied Science), BT-9 (manufactured by Nikko Chemicals Co., Ltd.), Brij (trademark) 35 (manufactured by Merck Ltd.), and Brij (trademark) 52 (manufactured by Merck Ltd.), respectively.

In the treatment liquid 2 as used herein, the concentration of the buffer is from 0.05 M to 1 M, preferably from 0.1 M to 0.5 M, the concentration of the chelating agent is from 0.001 M to 0.1 M, preferably from 0.005 M to 0.05M, and the concentration of the surfactant is from 0.0001% (Vol./Vol.) to 2% (Vol./Vol.), preferably from 0.001% (Vol./Vol.) to 1% (Vol./Vol.). The treatment liquid 2 may contain, in addition to the buffer, the chelating agent, and the surfactant, anything that does not impair the purpose of the step (c), and may contain, for example, an additive, such as a preservative or an antiseptic. Specific examples of the preservative and the antiseptic are as described above. The treatment liquid 2 is more specifically exemplified by a solution containing 20 mM EDTA and 0.2% (Vol./Vol.) TRITON X-100 ain 200 mM TES-NaOH (pH 7.0).

The step (d) is a step of centrifuging the solution obtained in the step (c) to collect a podocalyxin-solubilized liquid in which the podocalyxin of the urinary sediment has been solubilized. The centrifugation in this step may be performed through use of a centrifuge with agravity acceleration (G) set to from 5,000 g to 20,000 g, preferably from 10,000 g to 15,000 g. The target product of this step is a supernatant obtained after the centrifugation. The supernatant contains solubilized podocalyxin derived from the podocytes and the podocyte fragments. In this step, after the centrifugation, the supernatant is collected. The podocalyxin-solubilized liquid that is the supernatant obtained in this step is referred to as "urinary sediment sample liquid" in the present invention. The pH of the urinary sediment sample liquid is not particularly limited, but is preferably adjusted to from 5.5 to 7.0. When the pH falls within the range, an error in test value is reduced.

The urinary sediment sample liquid may be specifically prepared in the following manner. In the step (a), 100 µL of the treatment liquid 1 and 900 µL of the urine specimen are mixed, and in the step (b), the mixed liquid of the step (a) is centrifuged (1,500 g, 4° C., 5 min) to provide urinary sediment containing podocytes and podocyte fragments. Then, in the step (c), the urinary sediment containing podocytes and podocyte fragments, and 100 µL of the treatment liquid 2 are mixed, and in the step (d), the mixed liquid of the step (c) is centrifuged (15,000 g, 4° C., 5 min) to collect the supernatant. Thus, the urinary sediment sample liquid that is the podocalyxin-solubilized liquid can be obtained.

As a method of detecting podocalyxin from the urinary sediment sample liquid itself, a known method and any method to be developed in the future may be used. An example of the method of detecting the podocalyxin of the urinary sediment sample liquid is an immunological technique. The immunological technique may be performed, for example, by an immunostaining method (including a fluorescent antibody method, an enzymatic antibody method, a heavy metal-labeled antibody method, and a radioisotope-labeled antibody method), a combination of separation based on an electrophoresis method and a detection method with fluorescence, an enzyme, a radioisotope, or the like (including a western blot method and a fluorescent two-dimensional electrophoresis method), enzyme-linked immunosorbent assay (ELISA), a dot blotting method, latex agglutination-turbidimetric immunoassay (LA), or immunochromatography. Of those, an ELISA method or an LA method is preferably used. Among ELI SA methods, a sandwich method is preferably used from the viewpoint of quantitativity. In the sandwich method, the urinary sediment sample liquid is added to a microtiter plate having immobilized thereon an anti-podocalyxin antibody to cause an antigen-antibody reaction, an enzyme-labeled anti-podocalyxin antibody is further added to cause an antigen-antibody reaction, the plate is washed and then subjected to a reaction with an enzyme substrate and color development, and an absorbance is measured.

In the present invention, the antibody to be used for detecting podocalyxin may be any antibody capable of specifically detecting podocalyxin. The anti-podocalyxin antibody to be used in the present invention may be a known antibody, or may be an antibody to be developed in the future, and is not particularly limited. Examples of the anti-podocalyxin antibody in the present invention include a monoclonal antibody, a polyclonal antibody, a labeled antibody, a chimeric antibody, a humanized antibody, and binding active fragments thereof.

Through detection of podocalyxin in the urinary sediment sample liquid, a podocalyxin concentration or amount in the urinary sediment sample liquid can be calculated. Such podocalyxin concentration or amount in the urinary sediment sample liquid is referred to as podocalyxin value in the urinary sediment sample liquid. Through correction of the podocalyxin value in the urinary sediment sample liquid with a value for a urinary component to be stably excreted into the urine (urinary component value), a podocalyxin excretion amount in the urinary sediment can be obtained. The urinary component is preferably urinary creatinine. The urinary creatinine is considered to be nearly constant in one individual irrespective of a disease because the production of creatinine depends on the amount of muscles. In the examination of a urinary excreted substance, in order to avoid an error in urine volume, a technique involving correcting the amount of the urinary excreted substance of interest into an amount per g of creatinine is generally used. With this, amounts of the urinary excreted substance per unit gram of creatinine can be compared to each other. The podocalyxin excretion amount (PCX/Cre) in the urinary sediment when the urinary component is urinary creatinine may be calculated by the following equation.

<Equation>PCX/Cre: Podocalyxin excretion amount
in urinary sediment (ng/mg)=100 xpodocalyxin
concentration in urinary sediment sample liquid
(ng/mL)÷urinary creatinine concentration(mg/
dL)

Through use of the podocalyxin excretion amount (PCX/Cre) in the urinary sediment of the test subject, the number of urinary podocytes of the test subject can be calculated. The number of urinary podocytes of the test subject obtained by the present invention is estimated from podocalyxin derived from podocytes present as cells in the urine, and podocalyxin derived from fragments of podocytes present not as cells but as fragments. Accordingly, in order to estimate the number of urinary podocytes, it is necessary to determine, by calculation, how large the number of podocytes from which the fragments of podocytes are derived is. The number of urinary podocytes of the test subject is calculated using a podocalyxin amount derived from one podocyte. The podocalyxin amount derived from one podocyte (podocalyxin amount per podocyte) may be calculated by any method, and may be calculated using the amount of podocytes excreted into the urine of a renal disease patient and the podocalyxin excretion amount in the urinary sediment of the renal disease patient. The podocalyxin amount derived from one podocyte is from 10 pg to 1,000 pg, preferably from 100 pg to 200 pg. Now, the method of calculating the podocalyxin amount derived from one podocyte is specifically exemplified. Each numerical value to be used for the estimation method including the following calculation method (e.g., a reduction in the number of podocytes in the kidneys of the renal disease patient) is not limited to a specific numerical value described herein, and when more accurate measurement is made possible along with the progress of science, a measured value obtained by such measurement may be used as each numerical value.

First, the amount of podocytes excreted into the urine of the renal disease patient is calculated on the basis of a reduction in the number of podocytes in the kidneys of the renal disease patient. It has been reported in Non Patent Literature 5 above that the number of podocytes per glomerulus reduced from 544 to 475 over 3 years in diabetes patients having proteinuria (micro/macroalbuminuria). In other words, the podocytes of the diabetes patients having proteinuria (micro/macroalbuminuria) reduced by 12.68% per glomerulus (100×(544-475)/544=12.68). Through use of such reduction ratio of podocytes per glomerulus in the diabetes patients, i.e., 12.68%, the reduction in the number of podocytes from the kidneys is calculated. In this connection, a healthy subject without nephrectomy or the like has two kidneys, and there is a report that there are 600,000 glomeruli in each kidney with 300 podocytes per glomerulus (Non Patent Literature 2). Accordingly, there are 600,000×2×300=360,000,000 podocytes in the kidneys. The number of podocytes per glomerulus is not limited to 300, and when measurement of a more accurate number is made possible along with the progress of science, such value may be used. The number of podocytes lost from the kidneys of a diabetes patient is 360,000,000×0.1268=45,648,000, i.e., the number of podocytes lost from the kidneys of the diabetes patient over 3 years is calculated to be 45,648,000. The numbers of podocytes lost from the kidneys over 1 year and 1 day are considered to be 15,216,000 and 41,688, respectively, and assuming that the podocytes lost from the kidneys have been excreted into the urine, the urine contains 41.7 podocytes per mL (when a daily urine volume is assumed to be 1,000 mL) or 41.7 podocytes per mg of creatinine (when daily creatinine excretion is assumed to be 1 g). In other words, it is calculated that a diabetes patient having proteinuria (micro/macroalbuminuria) excretes 41.7 podocytes/mg of creatinine into the urine. Herein, a diabetes patient exhibiting proteinuria (micro/macroalbuminuria) is referred to as diabetic nephropathy patient.

Next, the podocalyxin excretion amount in the urinary sediment of the renal disease patient is calculated. As described above, the podocalyxin excretion amount in the urinary sediment can be calculated by obtaining the urinary sediment sample liquid through use of the urine specimen collected from the renal disease patient. As a specific example, 6.07 ng/mg, which is average PCX/Cre in urinary sediment sample liquids of diabetic nephropathy patients (micro/macroalbuminuria) calculated in Examples to be described later, is used.

The podocalyxin amount derived from one podocyte is calculated from the amount of podocytes excreted into the urine of the renal disease patient and the podocalyxin excretion amount in the urinary sediment of the renal disease patient. The average podocalyxin amount of the urinary sediment sample liquids per mg of creatinine in the diabetic nephropathy patients (micro/macroalbuminuria) is 6.07 ng, and the number of podocytes is 41.7. Accordingly, 6.07/41.7=0.146 ng (=146 pg), i.e., the podocalyxin amount derived from one podocyte is calculated to be 146 pg.

In the present invention, the number of urinary podocytes of the test subject can be estimated by calculating the number of urinary podocytes through use of the podocalyxin excretion amount in the urinary sediment of the test subject and the podocalyxin amount derived from one podocyte (podocalyxin amount per podocyte). That is, the number of urinary podocytes of the test subject can be calculated by dividing the podocalyxin excretion amount in the urinary sediment sample liquid of the test subject by the podocalyxin amount derived from one podocyte. The podocalyxin excretion amount in the urinary sediment sample of the test subject is obtained through correction with the value for the urinary component to be stably excreted into the urine (urinary component value), and hence the number of urinary podocytes of the test subject calculated by this method can be similarly calculated as the number of podocytes excreted into the urine corrected with the urinary component value.

A specific example of a method of calculating the number of urinary podocytes of the test subject is described using the values of podocalyxin excretion amounts (PCX/Cre) in urinary sediment obtained in Examples to be described later. In Examples to be described later, the average PCX/Cre in urinary sediment samples of diabetic nephropathy patients having microalbuminuria was 3.7 ng/mg, and the average PCX/Cre of diabetic nephropathy patients having macroalbuminuria was 8.8 ng/mL. Through use of those values of PCX/Cre, and the podocalyxin amount per podocyte (146 pg) derived in the foregoing, the numbers of podocytes excreted into urine were calculated. As a result, the number was calculated to be 25.3 (3.7/0.146=25.3) for the diabetic nephropathy patients having microalbuminuria, and the number was calculated to be 60.2 (8.8/0.146=60.2) for the diabetic nephropathy patients having macroalbuminuria.

According to the related-art fluorescent antibody method using an anti-podocalyxin antibody, 0.1 to 0.3 podocyte appears per mL of urine (or per mg of creatinine) in diabetic nephropathy (Non Patent Literature 2). Assuming that a daily urine volume is 1,000 mL, the number of podocytes to be excreted daily is calculated to be at a level of from 100 to 300. According to this calculation, the number of podocytes to be lost from glomeruli is calculated to be 200 (=100+300/2)×365 days=73,000 for 1 year, 730,000 for 10 years, and 2,190,000 for 30 years. Meanwhile, with reference to the number of glomeruli and the number of podocytes described in Non Patent Literature 2, a healthy subject without nephrectomy or the like has 3,600,000,000 podocytes in the kidneys. On the basis of the measurement results of the fluorescent antibody method, even if 2,190,000 podocytes are lost over 30 years in a diabetic nephropathy patient, 2,190,000/360,000,000=0.06 (6%) of the total number of podocytes of a human are only lost. Such reduction ratio is too low a value for the cause of kidney failure to be explained. Accordingly, it is considered that more podocytes than the number of urinary podocytes to be detected by the fluorescent antibody method appear in urine. The number of urinary podocytes calculated by the estimation method of the present invention is from 100 to 150 times larger than the numerical value obtained by the fluorescent antibody method. According to the number of urinary podocytes obtained by the estimation method of the present invention, 60.2×1,000×365×10=219,730,000 podocytes are shed into urine over 10 years in a patient with macroalbuminuria. This is about 61% of the total number of podocytes of a human, i.e., 360,000,000, and is a numerical value with which the cause of kidney failure can be explained. Accordingly, the number of urinary podocytes obtained by the estimation method of the present invention is considered to be an indicator more accurately reflecting the condition of a renal disease.

That is, the estimation method of the present invention can be used for an examination method for a renal disease. In an examination method of the present invention, a case in which the number of urinary podocytes calculated through detection of podocalyxin in the urinary sediment sample liquid is a certain number or more is assessed as having a renal disease. In addition, the severity of a renal disease can also be assessed based on the number of podocytes. As the number of podocytes becomes larger, the severity of a renal disease is assessed as being higher. Accordingly, the detection method of the present invention may be performed for the purpose of monitoring the progression of a renal disease in a renal disease patient.

The estimation method of the present invention may be used in the examination of a renal disease, and is preferably used in the examination of glomerular disease in which an abnormality is found in the glomerulus. Examples of the glomerular disease include diabetic nephropathy, IgA nephropathy, nephrotic syndrome, chronic glomerulonephritis, membranous nephropathy, ANCA-associated nephritis, systemic erythematosus (lupus nephritis), purpura nephritis, interstitial nephritis, crescentic nephritis, focal glomerulosclerosis, nephrosclerosis, acute kidney failure, chronic kidney failure, renal amyloidosis, scleroderma kidney, interstitial nephritis due to Sjogren's syndrome, and drug nephropathy.

The examination method of the present invention may be performed simultaneously with a related-art general urine examination, such as a medical check-up, or may be performed by collecting urine separately from a test subject suspected of having diabetes or a renal disease, or a patient diagnosed as having diabetes or a renal disease. In addition, the examination method of the present invention may be performed for the purpose of monitoring the onset or progression of diabetic nephropathy in a diabetes patient. In addition, the examination method of the present invention may also be performed for the purpose of monitoring the onset or progression of nephropathy in a patient suspected of having nephropathy.

The present invention also encompasses a reagent kit for urine treatment, for detecting podocalyxin in a urinary sediment sample liquid, the reagent kit including the following (a) to (c):

(a) a treatment liquid 1 containing a buffer and a chelating agent;

(b) a treatment liquid 2 containing a buffer, a chelating agent, and a surfactant; and (c) an anti-podocalyxin antibody.

EXAMPLES

Now, the present invention is more specifically described by way of Reference Example and Examples of the present invention. However, the present invention is by no means limited thereto, and various applications are possible without departing from the technical idea of the present invention.

(Reference Example 1) Podocalyxin Staining of Urinary Sediment by Fluorescent Antibody Method The detection of podocytes by a fluorescent antibody method was performed according to the following procedure.

(1) 30 mL of urine collected from a test subject was preserved in Urikeep 5D (Muto Pure Chemicals Co., Ltd.) containing 20 mL of a urine cell preservation liquid (time required: 1 minute to 2 minutes).

(2) An auto-smear sample was produced on a slide glass with CYTOSPIN (time required: 10 minutes).

(3) The produced auto-smear sample was air-dried (time required: 1 hour to 2 hours).

(4) The air-dried sample and an anti-podocalyxin antibody were subjected to a reaction by being left to stand still at room temperature for 1 hour (time required: 1 hour).

(5) After the reaction, the slide glass was washed three times with PBS (time required: 5 minutes).

(6) The sample on the slide glass and FITC-labeled anti-mouse IgG were subjected to a reaction by being left to stand still at room temperature for 1 hour (time required: 1 hour).

(7) After the reaction, the slide glass was washed three times with PBS (time required: 5 minutes).

(8) The sample on the slide glass was subjected to microscopic observation using a fluorescence microscope at a magnification of 100.

A photograph obtained by observation with a fluorescence microscope is shown in FIG. 1. In FIG. 1, one podocyte was found at the center (arrow), and PCX-positive fragments having various sizes (encircled parts) were found here and there.

Example 1

Preparation of Urinary Sediment Sample Liquid

A urinary sediment sample liquid was prepared by treating urine collected from a test subject in the following manner.

(1) 1,000 µL of the urine and 111 µL of a treatment liquid 1 (2 M TES-NaOH (pH 7.0), 0.2 M EDTA) were mixed with each other.

(2) The resultant mixed liquid was centrifuged (1,500 g, 4° C., 5 min).

(3) The supernatant after the centrifugation was discarded, and a pellet (sediment) was obtained. To the pellet, 100 µL of a treatment liquid 2 (200 mM TES-NaOH (pH 7.0), 20 mM EDTA, 0.2% (Vol./Vol.) TRITON X-100) was added, and the mixture was stirred with Voltex.

(4) The mixed liquid obtained after the stirring was centrifuged (15,000 g, 4° C., 5 min).

(5) After the centrifugation, the supernatant was collected, and used as the urinary sediment sample liquid.

Example 2

Measurement of Podocalyxin Excretion Amount in Urinary Sediment in Urinary Sediment Sample Liquid A podocalyxin concentration was measured using two kinds of anti-human podocalyxin monoclonal antibodies. Those two kinds of antibodies respectively recognize two different epitopes of human podocalyxin, and are respectively an anti-human podocalyxin monoclonal antibody a (hereinafter referred to simply as "antibody a") and an anti-human podocalyxin monoclonal antibody b (hereinafter referred to simply as "antibody b"). In this Example, an antibody a-immobilized microtiter plate (split type micro plate GF8 high: Nunc), and a horseradish peroxidase-labeled antibody b (hereinafter abbreviated as "HRP") were used.

First, 100 μL of the urinary sediment sample liquid prepared in Example 1 described above was added to wells of the antibody a-immobilized microtiter plate. The plate was left to stand still at 37° C. for 1 hour, and then the urine sample solution was removed from the wells by decantation. The wells were washed by adding a solution containing 3.6 mM $Na_2HPO_4$, 1.4 mM $KH_2PO_4$, 145 mM NaCl, and 0.05% (Vol./Vol.) TWEEN 20 (hereinafter abbreviated as "PBS-T solution") to the wells of the microtiter plate at 200 μL/well and removing the PBS-T solution by decantation. The washing step was performed a total of three times. After that, an HRP-labeled antibody b solution was added at 100 μL/well. The plate was left to stand still at 37° C. for 1 hour, and then the HRP-labeled antibody b solution was removed by decantation. Washing was performed by adding the PBS-T solution at 200 μL/well and removing the PBS-T solution by decantation. The washing step was performed a total of three times.

After that, TMB 1-STEP Substrate System (Dako) was used as a substrate solution for an HRP enzymatic reaction and added at 100 μL/well, and the plate was left to stand still under a light-shielding condition at 25° C. for 30 minutes. After that, a 313 mM $H_2SO_4$ solution was added at 100 μL/well as a reaction terminating solution, and each of the wells was measured for its absorbances at wavelengths of 450 nm and 630 nm using MULTISKAN Ascent and Ascent Software for MULTISKAN (Dainippon Pharmaceutical Co., Ltd.). Then, a value obtained by subtracting the absorbance at a wavelength of 630 nm from the absorbance at a wavelength of 450 nm was defined as a measured value. Native human podocalyxin extracted from the kidney was used as a standard for a calibration curve to derive a podocalyxin concentration in the urinary sediment sample liquid. A podocalyxin excretion amount in urinary sediment obtained by correcting the podocalyxin concentration with a urinary creatinine concentration was calculated from the following equation.

<Equation>PCX/Cre: Podocalyxin excretion amount in urinary sediment (ng/mg)=100×podocalyxin concentration in urinary sediment (ng/mL)÷urinary creatinine concentration(mg/dL)

Example 3

Measurement of Podocalyxin Excretion Amount in Urinary Sediment Sample Liquid of Diabetic Nephropathy Patient With use of urine specimens collected from 32 diabetes patients having urine protein (microalbuminuria: 17 patients, macroalbuminuria: 15 patients), urinary sediment sample liquids were prepared by the method of Example 1. With use of the resultant urinary sediment sample liquids, podocalyxin in the urinary sediment sample liquid derived from each diabetes patient was detected and a podocalyxin excretion amount was calculated by the method of Example 2. The results are shown in Table 1.

TABLE 1

Podocalyxin Excretion Amount in Urinary Sediment of Diabetic Nephropathy Patient having Proteinuria

| No. | PCX/Cre (ng/mgCre) |
| --- | --- |
| 1 | 2.0 |
| 2 | 0.0 |
| 3 | 2.8 |
| 4 | 1.5 |
| 5 | 2.2 |
| 6 | 2.3 |
| 7 | 1.9 |
| 8 | 5.8 |
| 9 | 1.3 |
| 10 | 6.2 |
| 11 | 15.5 |
| 12 | 1.7 |
| 13 | 13.0 |
| 14 | 0.0 |
| 15 | 2.3 |
| 16 | 1.3 |
| 17 | 2.7 |
| 18 | 6.0 |
| 19 | 2.6 |
| 20 | 1.1 |
| 21 | 0.6 |
| 22 | 8.5 |
| 23 | 0.0 |
| 24 | 7.9 |
| 25 | 0.1 |
| 26 | 21.0 |
| 27 | 0.0 |
| 28 | 28.8 |
| 29 | 1.6 |
| 30 | 4.8 |
| 31 | 42.8 |
| 32 | 5.9 |
| Average (microalbuminuria) | 3.7 |
| Average (macroalbuminuria) | 8.8 |
| Average (overall) | 6.07 |

No. 1 to 17: diabetic nephropathy patients having microalbuminuria
No. 18 to 32: diabetic nephropathy patients having macroalbuminuria Example 4

Estimation of Number of Urinary Podocytes of Test Subject (1) Calculation of Podocalyxin Amount Derived from one Podocyte It has been reported in Non Patent Literature 5 that the number of podocytes per glomerulus reduced from 544 to 475 over 3 years in diabetes patients having proteinuria (micro/macroalbuminuria). On the basis of this report, it is considered that the podocytes of the diabetes patients having proteinuria reduced by 12.68% per glomerulus. When the podocyte reduction of 12.68% per glomerulus is applied to the number of podocytes (360,000,000) in the kidneys of a healthy subject, the number of podocytes lost over 3 years is calculated to be 45,648,000 (36,000,000×0.1268=45,648,000). The number is 15,216,000 for 1 year, 41,688 for 1 day, 41.7 per mL (when a daily urine volume is assumed to be 1,000 mL), or 41.7 per mg of creatinine (when a daily creatinine excretion amount is assumed to be 1 g).

In Example 3, the average podocalyxin excretion amount (PCX/Cre) in the urinary sediment sample liquids of the diabetic nephropathy patients having proteinuria was found to be 6.07 ng/mg. In the diabetic nephropathy patients having proteinuria, the podocalyxin amount in the urinary sediment samples per mg of creatinine is 6.07 ng, and the number of podocytes is 41.7. Accordingly, a podocalyxin amount derived from one podocyte is 146 pg (6.07/41.7=0.146 ng (146 pg)).

(2) Calculation of Number of Podocytes in Urine Collected from Test Subject

In Example 3, the average PCX/Cre in the urinary sediment sample liquids of the diabetic nephropathy patients having microalbuminuria was determined to be 3.7 ng/mg, and the average PCX/Cre in the urinary sediment sample liquids of the diabetic nephropathy patients having macroalbuminuria was determined to be 8.8 ng/mL. Through use of the results of PCX/Cre, and the podocalyxin amount per podocyte (146 pg) derived in the foregoing, the numbers of podocytes excreted into urine were calculated. As a result, the number was calculated to be 25.3 (3.7/0.146=25.3) for the diabetic nephropathy patients having microalbuminuria, and the number was calculated to be 60.2 (8.8/0.146=60.2) for the diabetic nephropathy patients having macroalbuminuria.

The number of podocytes detected by the related-art fluorescent antibody method as described in Reference Example 1 was from 0.1 to 0.3 per mL of urine or per mg of creatinine. Accordingly, it was found that the number of urinary podocytes calculated by the method of the present invention was from 100 to 150 times larger than the number of urinary podocytes calculated by the related-art fluorescent antibody method. According to the method of the present invention, it is estimated that 219,730,000 podocytes are shed into urine over 10 years in a diabetic nephropathy patient having macroalbuminuria (60.2×1,000×365×10=219,730,000). Such number of urinary podocytes over 10 years is about 61% of the total number of podocytes of a human, i.e., 360,000,000. It was considered that the estimation method of the present invention enabled more accurate estimation of the true total number of podocytes shed into urine than the related-art fluorescent antibody method.

INDUSTRIAL APPLICABILITY

As compared to the number of urinary podocytes obtained through detection with a fluorescence microscope by the fluorescent antibody method serving as a related-art method, the number of urinary podocytes calculated through detection of podocalyxin in the urinary sediment sample liquid by the estimation method of the present invention more accurately reflects symptoms of a renal disease. Accordingly, the number of urinary podocytes calculated by the estimation method of the present invention allows efficient prediction of the onset of a renal disease, a therapeutic effect thereon, the degree of podocyte injury, and a prognosis, and can be suitably used as a diagnostic material for a renal disease. The examination method for a renal disease using the estimation method of the present invention allows a therapeutic strategy to be appropriately decided, and hence is useful also for a patient. In addition, the estimation method of the present invention can be carried out simply and rapidly, and hence is advantageous.

The invention claimed is:

1. A method of determining a number of urinary podocytes comprising detecting podocalyxin in a urinary sediment sample liquid and further comprising calculating a number of urinary podocytes through use of a podocalyxin excretion amount in the urinary sediment sample liquid and a podocalyxin amount per podocyte, wherein the method comprises the following steps (1)-(3):
   (1) a step of preparing the urinary sediment sample liquid by separating urinary sediment from urine collected from a test subject, wherein said urine is treated by following steps (a)-(e):
   (a) a step of adding and mixing, into urine collected from a test subject, a treatment liquid 1 consisting of a buffer and a chelating agent;
   (h) a step of centrifuging in a condition of 800-2500 g a solution obtained in the step (a) to separate urinary sediment;
   (c) a step of adding and mixing, into the urinary sediment obtained in the step (b), a treatment liquid 2 consisting of a buffer, a chelating agent and a surfactant;
   (d) a step of centrifuging in a condition of 10000-15000 g a solution obtained in the step (c) to separate urinary sediment from supernatant;
   (e) a step of recovering the supernatant obtained in the step (d) as a urinary sediment sample liquid,
   (2) a step of measuring a podocalyxin excretion amount in the urinary sediment sample liquid through detection of podocalyxin in the urinary sediment sample liquid using two kinds of anti-human podocalyxin monoclonal antibodies being able to recognize two different epitopes of human podocalyxin; and
   (3) a step of calculating the number of urinary podocytes by dividing the podocalyxin excretion amount in the urinary sediment sample liquid by a podocalyxin amount per podocyte.

2. A method for determining number of urinary podocytes in a urine sample from a subject, comprising treating a urine sample collected from a subject in order to prepare a urinary sediment sample liquid for testing for the presence of podocyte comprising:
   (a) combining the urine sample with a solution comprising a buffer and a chelating agent without surfactant to obtain a urine mixture in which the of the urine mixture is adjusted to pH 7;
   (b) centrifuging the urine mixture at 800-2500 g to obtain urinary sediment;
   (c) combining the urinary sediment with a solution comprising a buffer, a chelating agent and a surfactant to obtain a sedimentary mixture in which the pH of the sedimentary mixture is adjusted to pH 7;
   (d) centrifuging the sedimentary mixture at 10000-15000 g to obtain its supernatant;
   (e) recovering the supernatant as the urinary sediment sample liquid; and
   (f) detecting podocalyxin in the urinary sediment sample liquid to obtain a podocalyxin excretion amount, and estimating the number of urinary podocytes in the urine sample based on the podocalyxin excretion amount.

3. The method of claim 2, wherein anti-podocalyxin monoclonal antibody is used to detect podocalyxin.

4. The method of claim 3, wherein two kinds of anti-human podocalyxin monoclonal antibodies able to recognize two different epitopes of human podocalyxin are used.

5. The method of claim 2, wherein estimating the number of urinary, podocytes is performed by dividing the podocalyxin excretion amount in the urinary sediment sample liquid by an amount of podocalyxin known to be present in a podocyte.

6. The method of claim 2, wherein in (a) the solution consists of a buffer and a chelating agent.

7. The method of claim 2, wherein in (c) the solution consists of a buffer, chelating agent and surfactant.

8. The method of claim 2, wherein in (a) the solution consists of a buffer and chelating agent, and in (c) the mixture consists of a buffer, chelating agent and surfactant.

* * * * *